United States Patent [19]

Giocobbe et al.

[11] Patent Number: 4,981,980
[45] Date of Patent: Jan. 1, 1991

[54] DRUG FOR TREATING MANIC DEPRESSION

[75] Inventors: Robert A. Giocobbe, Lavellette; Leeyuan Huang, Watchung; Yu L. Kong, Edison; Yiu-Kuen T. Lam, Plainsboro, all of N.J.; Sagrario M. Del Val, Pez Volador, Spain; Carol F. Wichmann, Westfield; Deborah L. Zink, Manalapan, both of N.J.

[73] Assignee: Merck & Co., Inc., Rahway, N.J.

[21] Appl. No.: 407,162

[22] Filed: Sep. 14, 1989

[51] Int. Cl.$^5$ .................. C07D 307/94; A61K 31/34
[52] U.S. Cl. ...................................................... 549/345
[58] Field of Search ................. 549/345; 514/462, 469

[56] References Cited

U.S. PATENT DOCUMENTS

| | | | |
|---|---|---|---|
| 3,413,315 | 11/1968 | Stein et al. | 549/345 |
| 4,229,466 | 10/1980 | Miyazaki et al. | 549/345 |
| 4,263,317 | 4/1981 | Martin et al. | 549/345 |
| 4,831,053 | 5/1989 | Shinohara et al. | 514/462 |

OTHER PUBLICATIONS

Kaise et al., J. Chem. Soc. Chem. Comm. (1979), 726–727.

Primary Examiner—Glennon H. Hollrah
Assistant Examiner—Ba K. Trinh
Attorney, Agent, or Firm—William H. Nicholson; Joseph F. DiPrima

[57] ABSTRACT

Fermentation of a nutrient medium by a Hypomycetes fungus of the genus Memnoniella or Stachybotrys yields a product with a major component of structural formula I:

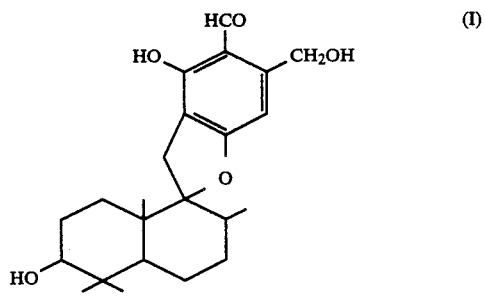

which is an inositol monophosphate phosphatase inhibitor and thereby useful in the treatment of manic depression.

2 Claims, 1 Drawing Sheet

DRUG FOR TREATING MANIC DEPRESSION

SUMMARY OF THE INVENTION

This invention is concerned with a novel compound of structural formula I:

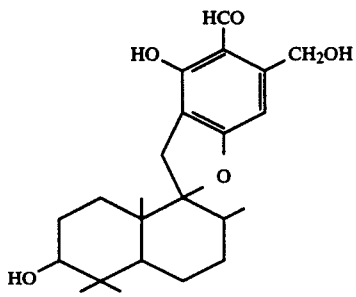

useful in the treatment of manic depression.

The invention is also concerned with the fermentation process by which the novel compound is Produced, and a novel Memnoniella sp. of microorganism used in that fermentation process.

This invention is further concerned with the use of the novel compound in treating manic depression and pharmaceutical formulations comprising the novel compounds as active ingredient.

BACKGROUND

Although lithium carbonate was discovered to be an effective antimanic agent by John Cade in 1949, it was not approved for general use in the U.S. until 1969. Lithium is highly specific in its alleviation of manic symptoms, normalizing the mood of manic patients rather than compensating for the excesses of the manic state through sedation or "tranquillization". In addition, it is perhaps the only drug in psychiatry for which clear prophylaxis against disease recurrences and deterioration has been demonstrated. Recent evidence suggests that lithium may also be effective in treating nonbipolar depressive illness and even in the treatment of psychotic disorders other than mania. However, its clearest effects are in bipolar disorder. Bipolar disorder includes both mania and depression, or only mania. Bipolar has been further divided into Bipolar I and II. In the former cases, there is presence of a full-blown manic episode, and in the latter case there is mild hypomania only.

Despite its remarkable and undisputed therapeutic properties, a number of issues detract from the therapeutic utility of lithium. Antipsychotic drugs are the first pharmacologic mode of treatment of acute bipolar disorder, unless the patient is manageable enough to wait the 7-10 days it takes for lithium to exert its antimanic effect. A costly prelithium workup is required because of the adverse effects common to lithium therapy. Lithium can cause a transient leukocytosis, can cause patients with a borderline thyroid reserve to become clinically hypothyroid, and can decompensate cardiac status due to shifts in fluids and electrolytes. Notably, the polyuria-polydipsia syndrome occurs in up to 60% of treated patients. Structural lesions in kidney, including interstitial fibrosis, tubular atrophy and glomerular sclerosis, are reported after chronic lithium treatment, especially in patients who have experienced lithium toxicity. Other adverse effects of lithium include tremor, weight gain, diarrhea and skin rash. These side effects are serious practical deterrents to the use of lithium in clinical practice.

Side effects, especially the more serious ones, can be reduced by monitoring plasma lithium concentrations in bipolar patients. The need to monitor plasma drug concentrations, and to maintain these within a narrow therapeutic range, detract from its clinical utility.

An ideal lithium mimetic agent would have a rapid onset of action in both bipolar and non-bipolar depression, require only once-a-day dosing, and have a safety profile requiring no extensive pretreatment medical evaluation, no plasma drug monitoring, nor be associated with as severe a spectrum of side effects as lithium, per se.

The identification of the phosphoinositide (PI) cycle as a likely target for lithium action arose from the work of Sherman and colleagues, who demonstrated a profound elevation of inositol-1-phosphate and a corresponding decrease in free inositol in the brains of rats treated systemically with lithium. This was attributed to inhibition of inositol-1-phosphate phophatase and led to the hypothesis that lithium was able to damp down the activity of the PI cycle in overstimulated cells, thus possibly explaining its effectiveness in the control of mania. An attraction of the hypothesis is that it was able to offer an explanation for the CNS selectivity of lithium action. Provision of inositol for the PI cycle can come from hydrolysis of inositol phosphates, by de novo synthesis from glucose, or from the diet. The former processes are dependent on the operation of inositol-1-phosphate phosphatase and are, therefore, inhibited by lithium. Dietary inositol can bypass lithium blockade in peripheral tissues but not in the CNS, since inositol does not cross the blood brain barrier. Thus, the increase in inositol-1-phosphate in brain is accompanied by an equivalent decrease in free inositol.

It appears that lithium interferes with inositol polyphosphate second messenger production and breakdown in animals. There is substantial support for this idea from work with isolated cells and tissues. Thus development of potent and specific inhibitors of inositol monophosphate phosphatase, could lead to completely novel drugs effective for the treatment of mania and depression.

Hydrolysis of the second messenger D-Ins(1,4,5)P$_3$ proceeds through D Ins(1,4)P$_2$ and D-Ins(4)P. The putative second messenger D-Ins(1,3,4,5)P$_4$ is hydrolysed in a similar way to D-Ins(3,4)P$_2$ via D-Ins(1,3,4)P$_3$ and then to D-Ins(3)P. Inositol-1-phosphate phosphatase, from bovine brain, purified to homogeneity is shown to be responsible for the hydrolysis, not only of D-Ins(1)P, but also of D-Ins(3)P (the intermediate for synthesis of inositol from glucose-6-phosphate, also known as L-Ins(1)P), D-Ins(4)P and its unnatural enantiomer, L-Ins(4)P. The enzyme is non-competitively inhibited by lithium and kinetic studies are compatible with binding of lithium to a phosphoenzyme intermediate, preventing its hydrolysis.

Kaise et al in *J. C.S. Chem. Comm.* (1979) p. 726-7 describes K-76 an inhibitor for the complement system which participates in rheumatoid arthritis, glomerulonephritis and other immune complex diseases. K-76 was obtained from Stachybotrys complementi nom. nud. sp. K-76 and has the structure:

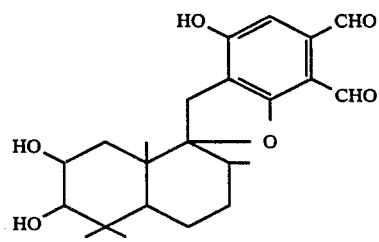

(II)

DETAILED DESCRIPTION OF THE INVENTION

Figure 1:
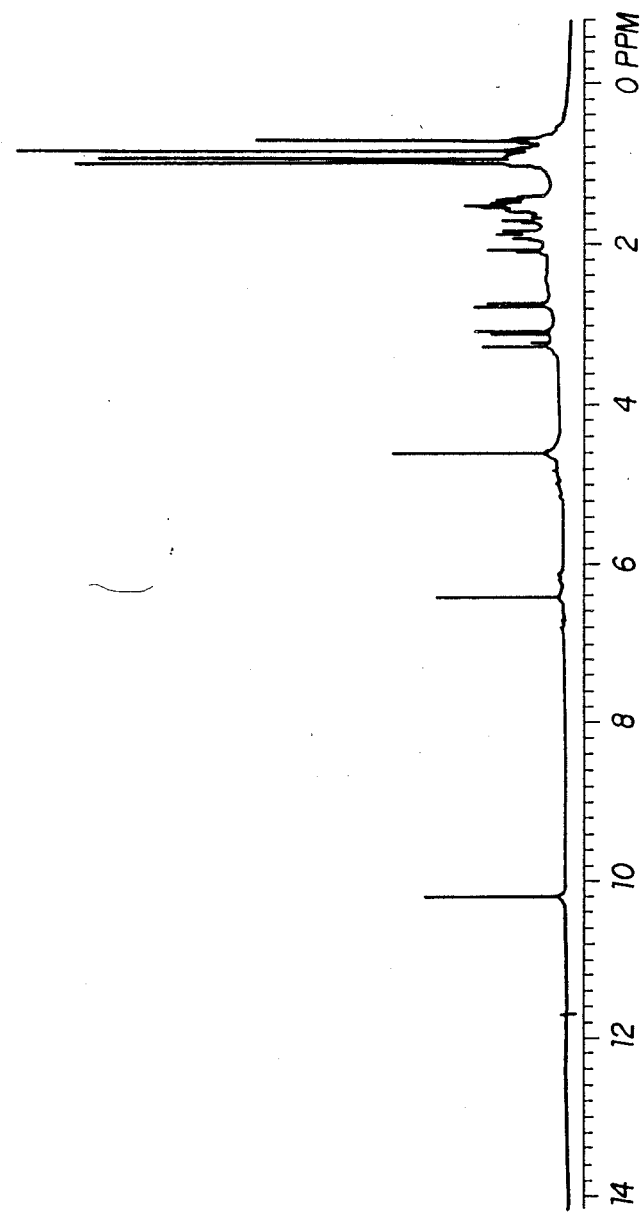

It has been found that fermentation with a fungus of the Memnoniella or Stachybotrys genus under certain conditions results in a complex of fermentation products, the major component of which is the novel compound of structural formula I:

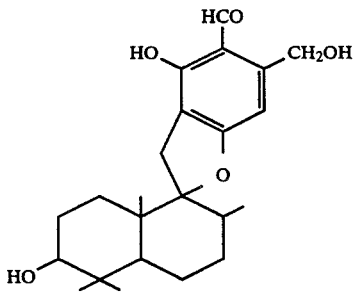

(I)

The structure for Compound I was assigned based upon the interpretation of the $^1$H NMR, $^{13}$C-NMR and mass spectral data shown below:

$^1$H-NMR Spectrum

FIG. 1 is a representation of the $^1$H-NMR spectrum of Compound I. The spectrum was recorded at 21° C. on a Varian XL-400 NMR spectrometer in CD$_3$CN. Chemical shifts are shown in ppm relative to TMS at zero ppm using the solvent peak at 1.93 ppm as internal standard. $^{13}$C-NMR Spectrum $^{13}$C-NMR spectrum were recorded at 21° C. on a Varian XL-400 NMR spectrometer in CD$_3$CN. Chemical shifts are reportd in ppm relative to TMS: 15.9, 16.4, 21.7, 22.7, 24.8, 25.9, 28.8, 31.3, 32.0, 37.7, 38.3, 41.0, 43.2, 64.2, 75.6, 100.9, 109.2, 110.6, 113.3, 146.2, 159.9, 169.9, and 189.5.

Mass Spectral Data

Mass spectra were recorded on a Finnigan-MAT 212 mass spectrometer in the electron impact mode (90 eV). High resolution exact mass measurements were performed on the same instrument using the peak matching method with perfluorokerosene as the internal standard. Trimethylsilyl (TMS) derivatives were formed using a 1:1 mixture of bistrimethylsilyltrifluoroacetamide (BSTFA)-pyridine at 50° C. for 10 minutes.

Compound I has the molecular weight 388 and forms a tri-TMS derivative. The following critical ions are observed in the EI mass spectrum of the underivatized compound:

| Found Mas (m/z) | Calculated | Formula |
|---|---|---|
| 388.2268 | 388.2250 | M$^+$, C$_{23}$H$_{32}$O$_5$ |
| 370 | — | M-H$_2$O |
| 207.1754 | 207.1749 | C$_{14}$H$_{23}$O |
| 189.1661 | 189.1643 | C$_{14}$H$_{21}$ |

-continued

| Found Mas (m/z) | Calculated | Formula |
|---|---|---|
| 180.0458 | 180.0423 | C$_9$H$_8$O$_4$ |
| 175.1503 | 175.1487 | C$_{13}$H$_{19}$ |
| 135.1180 | 135.1174 | C$_{10}$H$_{15}$ |

A preferred microorganism is of the genus, Memnoniella and preferably a *Memnoniella echinata* species especially the culture designated MF-5195 wt in the fungus collection of Merck & Co. Inc.

Other microorganisms useful in the novel process of this invention are *Memnoniella echinata*, MF 3686; *Stachybotrys chartarum*, MF 5217; and *Stachybotrys cylindrospora*, MF 5277.

The microorganism, MF5195wt was isolated from soil, and a sample of this living organism has been deposited without restriction in, and made a part of, the American Type Culture Collection, Rockville, Md., from which it is available under Accession Number ATCC No. 20928.

An examination of the cultural and morphological characteristics of ATCC No. 20928, was made according to the method described in *Myocology Guidebook*, (R. B. Stevens, Ed., 1981), University of Washington Press, Seattle. The data shown below confirm the designation of the culture ATCC No. 20928 as *Memnoniella echinata*. Differences are minor and of a strain differentiating nature.

The morphological characteristics of *Memnoniella echinata*, ATCC 20928, are as follows:

Colonies on corn meal agar effuse, hyaline at edges, soon darkening to dark grayish olive, Dark Olive, Dark Olive-Gray, Olive Gray, Iron Gray, Olivaceous Black, to Blackish Mouse Gray (capitalized color names from R. Ridgway, Color Standards and Nomenclature. 1912), sparse to velvety, with stroma and setae absent, composed of subaerial, appressed to slightly immersed mycelium. Mycelium composed of septate, branched, straight, flexuous, to contorted hyphae; hyphae hyaline to olive-gray in water, 1–4 um in diam.

Conidiophores macronematous, erect, determinate, unbranched straight to slightly curved, arising at right angles from a foot cell, 0- to 3-septate, 22–30 um$\mu$3.5–5 um, attenuated toward the apex, with a slight apical swelling; walls roughened due to granular pigmented surface, pale olive gray to olive-brown in water.

Conidiogenous cells phialidic, enteroblastic, discrete, reniform, in terminal whorls of 4–7, 8.5–11.5×3.5–6 um, without conspicuous collarettes.

Conidia globose to subglobose, rarely broadly elliptical in side view, 5.5–7×4.5–6.5 um, with punctate-verrucose ornamentation, usually biguttulate, olive-gray to grayish brown in water when mature, adhering in slimy masses at apices of young conidiogenous cells, soon drying and adhering together in chains.

This culture agrees well with the cultures described by Jong & Davis (Mycotaxon 3: 409–485) in their monograph of the genus Stachybotrys and Memnoniella.

The novel compound of this invention is useful as an anti manic agent at a dosage level of about 10–20 mg/kg/day, on a regimen of 1–4 times a day.

It is understood that the exact treatment level will depend upon the case history of the patient being treated and in the last analysis the precise treatment level falling within the above guidelines is left to the discretion of the therapist.

Also included within the scope of the present invention are pharmaceutical compositions comprising the novel compound of this invention. Preferably these compositions are in unit dosage forms such as tablets, pills, capsules, powders, granules, sterile parenteral solutions or suspensions, or suppositories for oral, parenteral or rectal administration. For preparing solid compositions such as tablets, the principal active ingredient is mixed with a pharmaceutical carrier, i.e., conventional tableting ingredients such as corn starch, lactose, sucrose, sorbitol, talc, stearic acid, magnesium stearate, dicalcium phosphate, gums, and other pharmaceutical diluents, e.g., water, to form a solid preformulation composition containing a homogeneous mixture. When referring to these preformulation compositions as homogeneous, it is meant that the active ingredient, is dispersed evenly throughout the composition so that the composition may be readily subdivided into equally effective unit dosage forms such as tablets, pills, capsules, and the like. This solid preformulation composition is then subdivided into unit dosage forms of the type described above containing from 50 to about 350 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release.

The liquid forms in which the novel composition of the present invention may be incorporated for administration orally or by injection include aqueous solutions, suitably flavored syrups, aqueous or oil suspensions, flavored emulsions with edible oils such as cottonseed oil, sesame oil, coconut oil, peanut oil and the like, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone, gelatin and the like.

For the production of the novel inositol monophosphate phosphatase inhibitor of this invention the present invention is not limited to the use of *Memnoniella echinata* ATCC 20928. It is especially desired and intended that there be included within the scope of this invention, the use of any Memnoniella or Stachybotrys sp., or natural or artificial mutants or variants produced from the described organism, or other variants thereof in so far as they can produce the novel inositol monophosphate phosphatase inhibitor of Structure I by the process of this invention. The artificial production of mutants may be achieved by conventional operations such as x-ray or untraviolet irradiation or by the use of chemical mutagens such as: nitrogen mustards, nitrosoguanidine and the like.

In a preferred embodiment of the present invention, the inositol monophosphate phosphatase inhibitor is produced by the aerobic cultivation of the *Memnoniella echinata* at a temperature range of from 25° C. to 30° C., preferably 25° C. Generally, the composition of the nutrient medium may be varied over a wide range. The essential nutrient ingredients are a carbon source and a nitrogen source. Other essential nutrients are provided via the mineral salts such as the chlorides, nitrates, sulfates, carbonates and phosphates of sodium, potassium, ammonium, magnesium and calcium. The nutrient medium may also contain sources of inorganic trace elements such as magnesium, iron, copper, manganese, zinc, cobalt, cadmium, molybdenum and the like. Cultivation has been found to be most productive in the pH range of from 6.0 to 8.0, most preferably at about 7.0.

Typical sources of carbon include: glucose, maltose, sucrose, dextrin, oil, starches, glycerol, mannitol and the like. Typical nitrogen sources include: ammonium sulfate; amino acids such as glycine, arginine, threonine, methionine; complex sources such as yeast autolysates, yeast hydrolysates, yeast cells, casein hydrolysate, malts, soy, cotton seed, tomato paste, corn steep liquor, yeast extract, and fermentation by-products such as whole yeast and distillers solubles.

The maximum yield of the phosphatase inhibitor can be achieved within about 2 to 22 days, usually in about 13-15 days of fermentation under optimum conditions.

The Inoculum

A 2 ml portion of a frozen culture ATCC 20928 in glycerol was defrosted and aseptically transferred to a 250 ml unbaffled Erlenmeyer flask containing 50 ml of sterile KF seed medium. The mixture was incubated at 28° C. on a 220 rpm, 2" throw shaker for 3 days.

When growth is abundant, usually 2-4 days, the culture growth may be used to inoculate a production medium.

Fermentation

Two ml of the growth medium were aseptically transferred to each of several unbaffled 250 ml. Erlenmeyer flasks containing 40 ml of medium. The fermentation conditions and yield of Compound I are as shown in the following table.

| Medium | Time | Conditions | Yield (mg/40 ml broth) |
|---|---|---|---|
| f4-sf | 14 days | 25° C., 220 rpm. | 104 |
| f4-sf | 14 days | 25° C., static | 87 |
| modified PBM | 18 days | 25° C., 220 rpm. | 383.2 |
| modified PBH | 18 days | 25° C., 220 rpm | 383.2 |
| modified PBN | 13 days | 25° C., 220 rpm. | 304 |
| modified PBN | 21 days | 25° C., 22 rpm. | 517 |

Media Compositions:

| 4f-sf | per 250 ml flask | fl-sf | per 250 ml flask |
|---|---|---|---|
| Millet | 15 g | Cracked corn | 10 g |
| Base liquid | 10 ml | Base liquid | 10 ml |

| *base liquid: | 1 liter |
|---|---|
| Ardamine pH | 0.2 gr |
| KH$_2$PO$_4$ | 0.1 gr |
| MgSO$_4$.7H$_2$O | 0.1 gr |
| Na tartrate | 0.1 gr |
| FeSO$_4$.7H$_2$O | 0.01 gr |
| ZnSO$_4$.7H$_2$O | 0.01 gr |
| Dist. H$_2$O | 1000 ml |
| pH: as is | |

| KF SEED MEDIUM | per liter | Trace Element Mix | per liter |
|---|---|---|---|
| Corn Steep Liquor | 5 g | FeSO$_4$.7H$_2$O | 1 g |
| Tomato Paste | 40 g | MnSO$_4$.4H$_2$O | 1 g |
| Oat flour | 10 g | CuCl$_2$.2H$_2$O | 25 mg |
| Glucose | 10 g | CaCl$_2$ | 100 mg |
| Trace Element | 10 ml | H$_3$BO$_3$ | 56 mg |

| -continued | | | |
|---|---|---|---|
| Mix | $(NH_4)_6Mo_7O_{24}.4H_2O$ | 19 | mg |
| pH = 6.8 | $ZnSO_4.7H_2O$ | 200 | mg |

| PBM modified: | | PBN modified: | |
|---|---|---|---|
| | 1 liter | | 1 liter |
| Glycerol | 75 gr | Glycerol | 85 gr |
| Corn steep liquor | 5 ml | Corn steep liquor | 5 ml |
| $(NH_4)_2SO_4$ | 2 gr | Corn meal | 10 gr |
| Lard Water | 5 gr | Lard Water | 5 gr |
| $CoCl_2.6H_2O$ | 10 mg | Soybean meal | 5 gr |
| P-2000 | 2 ml | P-2000 | 2 ml |
| Cod liver oil | 2 ml | Cod liver oil | 2 ml |
| Tomato paste | 5 gr | Tomato paste | 5 gr |
| Na citrate | 2 gr | Glycine | 2 gr |
| Dist. $H_2O$ | 1000 ml | Dist. $H_2O$ | 1000 ml |
| pH = 7.0 | | pH = 7.0 | |

| PBH modified: | |
|---|---|
| | 1 liter |
| Glycerol | 75 gr |
| Dextrose | 10 gr |
| $KH_2PO_4$ | 2 gr |
| Corn steep liquor | 5 ml |
| Pectin | 10 gr |
| Soybean meal | 5 gr |
| Cod liver oil | 2 gr |
| Tomato paste | 5 gr |
| Dist. $H_2O$ | 1000 ml |
| pH = 7.0 | |

Large Scale Fermentation

Approximately two percent inoculum was used to inoculate 2 liter Erlenmeyer flasks each containing 500 ml of the seed medium previously described. The second stage seed flasks were incubated at 28° C. for 24 hours on a rotary shaker at 220 rpm.

The production medium was adJusted to pH 7.0 with NaOH prior to sterilization. Four 14-L and two 22-L scale vessels contained sterile medium (10 liter and 15 liter working volume, respectively) consisting of glycerol 85.0 g/liter, corn steep liquor 5.0 ml/liter, corn meal 10.0 g/liter, lard water 5.0 g/liter, soybean meal 5.0 g/liter, cod liver oil 2.0 ml/liter, tomato paste 5.0 g/liter, glycine 2.0 g/liter and P-2000 antifoam (Dow) 2.0 ml/liter. Five percent inoculum was then inoculated into each fermentor. The fermentations were carried out at 25° . under a range of conditions for airflow (2.0–5.0 1/minute) and agitatiOn rate (200–500 rpm) for 96–118 hours.

Following fermentation, the accumulated Compound I may be recovered from the broth by conventional partition and chromatographic means. Generally, the broth is filtered through a filter aid to remove suspended solids, the filtrate is adjusted in pH and chromatography is employed to separate the active components.

Isolation of Compound I

Fermentation progress was monitored by analytical TLC (E. Merck silica gel 60F, 40% acetone/hexane, $R_f=0.35$) and HPLC (column: Whatman partisil 5 ODS-3 0.46×10 cm; mobile phase: 40% acetonitrile/water at 1 ml/min., k'=6.9; detection: UV at 215 nm). Eighty liters of broth from 6 fermentations were premixed with celite (4 kg), extracted with methylethylketone (96 liters), and filtered over a layer of celite and Whatman no. 3 filter paper. The upper organic layer of the filtrate was flash evaporated (under reduced pressure and below 35° C.) to give 183 g of crude extract. Differential pH partition of this crude was then performed as follows. The 183 g crude was redissolved in methylethylketone (2.4 liters) and washed with saturated aqueous sodium bicarbonate (2 liters). The organic layer was then extracted with 1 M NaOH(aq) (2×1.5 liters). The organic layer containing neutrals and bases was flash evaporated to a dry weight of 133.13 g. The aqueous layer was immediately neutralized with conc. HCl and extracted with methylethyl ketone (3.6 liters). The phenolic fraction was then flash evaporated to a dry weight of 34.35 g. Column chromatography of this phenolic extract on E. Merck silica gel 60 (0.040–0.063 mm; $V_b=2450$ ml) using 40% acetone/hexanes as the mobile phase at a flow rate of 50 ml/min was performed. Fractions of 200 ml each were collected. Anlytical TLC monitoring of effluent suggested the pooling of fractions 25 to 37 and 9 g of product was recovered.

What is claimed is:

1. An inositol monophosphatase inhibitor of the formula:

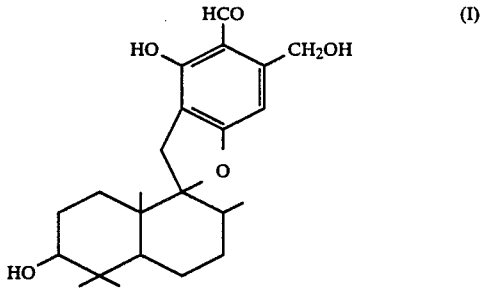

(I)

2. A pharmaceutical composition containing an effective amount of a monophosphate phosphatase inhibitor of claim 1 and a pharmaceutical carrier.

* * * * *

UNITED STATES PATENT AND TRADEMARK OFFICE
CERTIFICATE OF CORRECTION

PATENT NO. : 4,981,980

DATED : 1/01/91

INVENTOR(S) : Giacobbe, et al.

It is certified that error appears in the above-identified patent and that said Letters Patent is hereby corrected as shown below:

On the title page, under item [19] and in item [75], change "Giocobbe" to --Giacobbe--.

Signed and Sealed this

Nineteenth Day of May, 1992

Attest:

DOUGLAS B. COMER

Attesting Officer

Acting Commissioner of Patents and Trademarks